United States Patent [19]
DelRaso

[11] Patent Number: 5,508,174
[45] Date of Patent: Apr. 16, 1996

[54] METHOD AND MICRO ROLLER BOTTLE FOR IN VITRO EXPOSURE OF CELLS TO VOLATILE CHEMICALS

[75] Inventor: Nicholas J. DelRaso, Dayton, Ohio

[73] Assignee: The United States of America as represented by the Secretary of the Air Force, Washington, D.C.

[21] Appl. No.: 77,805

[22] Filed: Jun. 18, 1993

[51] Int. Cl.$^6$ .............................. C12Q 1/18; C12M 1/00; C12C 1/00; B01L 3/00
[52] U.S. Cl. .............................. 435/32; 435/31; 435/809; 436/63; 436/810; 422/102
[58] Field of Search .............................. 435/32, 31, 286, 435/287, 291, 292, 294, 296, 298, 302, 306, 809; 436/63, 810; 422/102

[56] References Cited

U.S. PATENT DOCUMENTS

| | | | |
|---|---|---|---|
| 3,932,222 | 1/1976 | Dorn | 435/296 |
| 4,062,652 | 12/1977 | Rolfo-Fontana | 435/296 |
| 4,337,104 | 6/1982 | Lynn | 435/296 |
| 4,717,668 | 1/1988 | Keilman et al. | 435/296 |
| 4,912,058 | 3/1990 | Mussie et al. | 435/285 |
| 4,935,371 | 6/1990 | Rickloff | 435/296 |
| 5,047,331 | 9/1991 | Swaine et al. | 435/29 |
| 5,075,234 | 12/1991 | Tunac | 435/286 |

FOREIGN PATENT DOCUMENTS

| | | |
|---|---|---|
| 2178447 | 2/1987 | United Kingdom . |

OTHER PUBLICATIONS

DelRaso et al, *The Toxicologist*, abstract of the 31st. Annual Meeting, 12(1), Abstract No. 986, Feb. 1992.
Sofuni et al, *Biological Abstracts*, vol. 81 No. 1, p. 385, Ref. No. 3450, 1984.
Watson, *In Vitro Methods of Toxicology*, CRC Press, pp. 182–184, 1992.
DelRaso et al, *Biological Abstract*, vol. 89, No. 5, p. 1038, Ref. No. 54349, 1989 (In vitro cell Dev Biol 25(11), 1031–10381 (1989).
DelRaso et al, "Novel In Vitro System . . . ", *The Toxicologist*, (12) 1, Feb. 1992, Abstract NR 986.
Olson et al "Modolation of Glucose . . . ", *Fund & Appl. Toxicology*, (15) pp. 270–80 (1990).
Nikula et al "Response of Rat . . . ", *Fund & Appl Toxicology*, (15), pp. 121–131 (1990).
Costa et al, "Toxicity of . . . ", *Toxicology & Appl. Pharm.* (95) pp. 241–247 (1988).
Dahlstrom-King, "Dose–Dependent . . . ", *Fund & Appl. Toxicology*, (14) pp. 833–841 (1990).
Watson (ed) "In Vitro Methods . . . " *CRC Press*, 1992, pp. 182–184.

*Primary Examiner*—Christina Y. Chan
*Assistant Examiner*—Abdel A. Mohamed
*Attorney, Agent, or Firm*—Charles E. Bricker; Thomas L. Kundert

[57] ABSTRACT

A culture bottle for the in vitro exposure of a cell culture to a volatile chemical comprises a closed cylindrical body defining a longitudinal axis and having an opening at each end of the body, substantially concentric with the axis, wherein each opening, comprises an aseptically sealable septum, wherein each opening has a diameter less than the diameter of the body. This bottle is used for the in vitro exposure of a cell culture to a volatile chemical by coating the inner surface of the culture bottle with the cell culture, adding a culture medium for the cells to the bottle, sealing both ends of the bottle, thereby enclosing a first atmosphere within the bottle, injecting a quantity of a second atmosphere containing the volatile chemical into the bottle through one of the septum while simultaneously providing egress for a like quantity of the first atmosphere from the bottle through one of the septum, incubating the cell culture, while rotating the bottle, for a suitable time, and determining the viability of the cell culture. Cells which do not or will not attach to the surface of the culture bottle may be attached to a carrier, such as a collagen-coated mesh and the cell-attached mesh disposed within the culture bottle.

2 Claims, 1 Drawing Sheet

METHOD AND MICRO ROLLER BOTTLE FOR IN VITRO EXPOSURE OF CELLS TO VOLATILE CHEMICALS

RIGHTS OF THE GOVERNMENT

The invention described herein may be manufactured and used by or for the Government of the United States for all governmental purposes without the payment of any royalty.

BACKGROUND OF THE INVENTION

This invention relates to the in vitro testing of volatile chemicals.

The toxic response of living organisms to organic chemicals is unpredictable. The safety of any chemical depends on factors such as route, time and frequency of administration, physical and chemical form of the material, dosage, acute as compared to chronic exposure, and the like.

The methods for testing and quantitizing toxic response include mass screening, either of a single chemical with a variety of organisms or a single organism with a variety of chemicals. The techniques for toxicity screening are generally well established.

The current technique for toxicity screening of volatile compounds, i.e., compounds which are in the gasous state at about 20° C. and 1 atm., particularly volatile compounds which are not soluble in aqueous media, has several drawbacks. The technique uses standard tissue culture plates, a sealed chamber, a rocker platform and a large capacity incubator. The culture plates containing the organism(s) under consideration are stacked in the sealed chamber. The chamber is filled with the volatile chemical under consideration. The chamber and the rocker platform are placed in the incubator where the organisms are incubated at a selected temperature for a desired time.

One limitation of this method is that measurement of disappearance of the volatile test compound cannot be accomplished due to the large ratio of head space volume to cell volume. Another limitation is that there is no assurance that all the test plates are exposed to the same concentration of test compound, particularly since the plates are generally stacked in the sealed chamber. A further drawback is that samples of medium cannot be taken from the plates without violating the integrity of the exposure conditions. Yet another limitation is that plastics which interact with the volatile test compound cannot be used in this method.

It is an object of the present invention to provide a culture bottle for the in vitro exposure of a cell culture to a volatile chemical which overcomes the above-listed drawbacks.

Another object of the present invention is to provide an improved method for the in vitro exposure of a cell culture to a volatile chemical.

Other objects and advantages of the invention will be apparent to those skilled in the art.

SUMMARY OF THE INVENTION

In accordance with the present invention there is provided a culture bottle for the in vitro exposure of a cell culture to a volatile chemical which comprises a closed cylindrical body defining a longitudinal axis and having an opening at each end of said body, substantially concentric with said axis, wherein each opening comprises aseptically sealable means, wherein each opening has a diameter less than the diameter of said body.

There is also provided a method for the in vitro exposure of a cell culture to a volatile chemical which comprises:

(a) providing a culture bottle comprising a closed cylindrical body defining a longitudinal axis and having aseptically sealable means at each end of said body, substantially concentric with said axis;

(b) coating the inner surface of said body with said cell culture;

(c) adding a culture medium for said cells to said bottle;

(d) sealing both ends of said bottle, thereby enclosing a first atmosphere within said bottle;

(e) injecting a quantity of a second atmosphere containing said volatile chemical into said bottle through one of said sealing means while simultaneously providing egress for a like quantity of said first atmosphere from said bottle through one of said sealing means;

(f) incubating said cell culture, while rotating said bottle, for a suitable time; and (g) determining the viability of said cell culture.

Cells which do not or will not attach to the surface of the culture bottle may be attached to a carrier, such as a collagen-coated mesh and the cell-attached mesh disposed within the culture bottle.

DETAILED DESCRIPTION OF THE INVENTION

Figure 1:
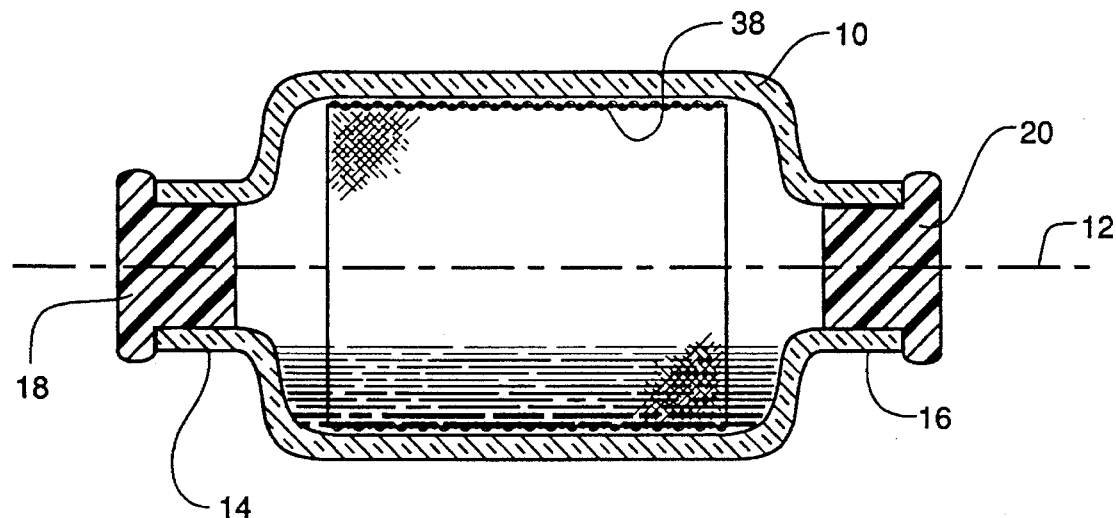
FIG. 1 is a sectional view of the device of this invention.

Referring to FIG. 1, the device of this invention comprises a closed cylindrical body 10 defining a longitudinal axis 12 having openings 14 and 16 at each end thereof, which openings are substantially concentric with axis 12. The openings 14 and 16 comprise aseptically sealable means 18 and 20, respectively. Each opening has a diameter less than the diameter of the body.

Body 10 is preferably transparent and should be fabricated from a material which is nonreactive, both with the organism(s) undergoing testing and with the test compound. A presently preferred material is an autoclavable (e.g., 250° C., 21 psi) glass, specifically one of the glasses commonly used in laboratory glassware, such as Pyrex®. Body 10 may also be fabricated from polymeric materials such as polyethylene, polypropylene, polycarbonate or the like.

Figure 2:
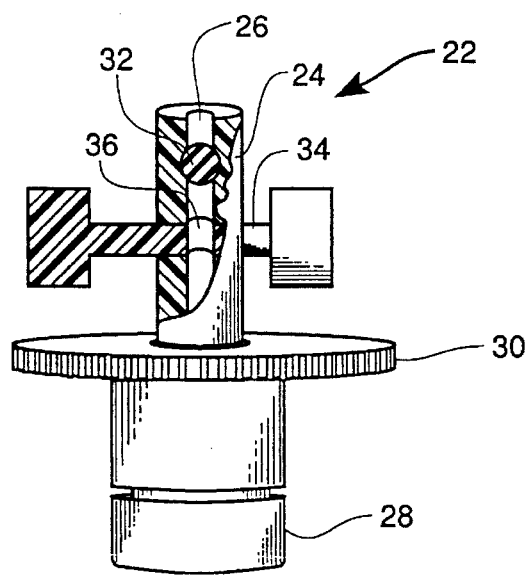
FIG. 2 is a side elevational view, partly in section, of a closure for the device shown in FIG. 1.

Sealable or sealing means 18 and 20 can be conventional rubber or polymeric septum stoppers. Because of the possible between such conventional materials and the test compound, it is presently preferred to use a closure device having a body which is inert to the test compound and which incorporates a septum and valve means. One such device is available commercially from Pierce, Rockford, Ill. under the tradename Mininert®. One form of a Mininert valve is shown in FIG. 2. Referring to FIG. 2, valve 22 comprises a cylindrical body 24 having a longitudinal bore 26, an expansible portion 28 for engagement with the opening to be sealed, screw means 30 for expanding portion 28, septum 32 and slide valve means 34 having a bore 36. In use, the expanding or expansible portion 28 is inserted into an opening 14 and the screw means 30 rotated to expand the portion 28 thereby securing valve 22 in opening 14. Opening 16 is sealed in like manner. To add or withdraw a sample to/from the body 10, the slide valve 34 is operated so that bore 36 aligns with longitudinal bore 26. A syringe needle, not shown, is inserted through the septum 32, the addition or withdrawal is made, the needle withdrawn and the valve is closed. All surfaces of valve 22 which are or may be exposed to the atmosphere within body 10 are fabricated from a polymeric material which is inert to the atmosphere, e.g., a polytetrafluoroethylene or a copolymer of hexafluoropropylene and tetrafluoroethylene.

Any adherent cell line or adherent primary cell type can be used in this system. Adherent cell lines may attach to glass walls, i.e., the inner surface of a glass body 10. When cells reach confluency, exposure can be initiated. Adherent primary cells do not divide and must be attached as a monolayer. This can be accomplished by attaching primary cells to a sterile strip of inert mesh 38, e.g., nylon mesh, precoated with an attachment factor such as collagen. The mesh is carefully rolled and placed into body 10 through one of the openings 14 or 16. After the mesh is unrolled within body 10, the openings 14 and 1.6 are sealed using the septa or the valve 22 previously described.

The collagen-coated mesh can be prepared as follows: Sterile mesh, 20 to 62 μm pore size, is placed into sterile tissue culture plates and collagen solution is evenly dispersed over the mesh. The plates are covered, then exposed to ammonia vapor for about 5 minutes to set the collagen gel. The mesh is washed at least twice to rid the collagen gel of cytotoxic ammonia.

The cells to be tested are washed and isolated using known procedures. The washed isolated cells are resuspended at a suitable cell density, e.g., about $10^6$ to $10^7$ /ml, in a suitable culture medium, e.g., Williams E or Leibovitz's-15. The culture medium may be supplemented with a suitable media supplement, e.g., fetal calf serum, dexamethasone, etc. The suspended cells are distributed over the mesh or over the inner surface of device 10. The cells are allowed to attach for a suitable period. If the mesh is used, it is rolled into a narrow tube, inserted into device 10 and allowed to unroll. Culture medium is added to the device 10 to a desired quantity. Sealing means 18 and 20 are inserted into openings 14 and 16. Device 10, containing the cells to be tested may be incubated for a suitable period to allow cells damaged during the isolation procedure to recover.

A syringe needle is inserted through one of the sealing means 18 or 20 to provide egress for excess atmosphere within device 10. A volatile compound of known concentration is injected, using a syringe, into device 10 through the other of the sealing means. After injecting the volatile compound, both needles are removed. A sample of the atmosphere within device 10 is taken from each device prepared for testing and analyzed by gas-chromatography (GC) to determine the actual concentration of the volatile compound in the device.

The thus-prepared test device is placed on a roller apparatus in an incubator at a suitable temperature. The device is rotated during incubation so that the cells are exposed to both the medium and the volatile compound. Samples of the medium may be taken for assay, such as cellular lactate dehydrogenase (LDH) or aspartate aminotransferase (AST), after predetermined times of exposure, through the sealing means, using a suitable syringe needle, without violating the experimental exposure conditions. At the termination exposure, a second sample of the atmosphere should be taken and analyzed by GC to ensure that the volatile compound is present at a concentration of at least about 95% of that measured initially.

The volatile compound test atmospheres are prepared in desired concentrations using known procedures. A control atmosphere of known concentration, e.g., 95% air/5% carbon dioxide, should also be prepared.

The method and apparatus of this invention can be used to rapidly screen volatile chemicals for potential in vivo toxicity.

The following example illustrates the invention:

EXAMPLE

Primary hepatocytes were exposed to 2,2-dichloro-1,1,1-trifluoroethane (HCFC-123), 1-chloro-1,2,2,2-trifluoroethane (HCFC-124), 1-chloro-1,1-difluoroethane (HCFC-142b) and an 80:20 mixture of HCFC-123 and HCFC-142b at 10,000, 100,000 and 500,000 ppm for 24 hours. The concentrations of the HCFC test agents were relatively stable over the 24 hr exposure period. Based on lactate dehydrogenase (LDH) and S-amino-transferase (AST) enzyme leakages, the relative rank ordering of toxicity was found to be HCFC-123>HCFC-123/142b>HCFC-124>HCFC-142b. These results correlated very well with results determined in vivo.

Various modifications may be made without departing from the scope of the appended claims.

I claim:

1. A method for the in vitro exposure of a cell culture to a volatile chemical which comprises:

(a) providing a culture bottle comprising a closed cylindrical body defining a longitudinal axis and having aseptically sealable system means at each end of said body, substantially concentric with said axis;

(b) coating the inner surface of said body with said cell culture;

(c) adding a culture medium for said cells to said bottle;

(d) sealing both ends of said bottle, thereby enclosing a first atmosphere within said bottle;

(e) injecting a quantity of a second atmosphere containing said volatile chemical into said bottle through one of said sealing means while simultaneously providing egress for a like quantity of said first atmosphere from said bottle through the other of said sealable means to avoid mixing of said first and second atmospheres;

(f) incubating said cell culture, while rotating said bottle, for a suitable time; and (g) determining the viability of said cell culture.

2. A method for the in vitro exposure of a cell culture to a volatile, chemical which comprises:

(a) providing a culture bottle comprising a closed cylindrical body defining a longitudinal axis and having aseptically sealable system means at each end of said body, substantially concentric with said axis;

(b) attaching said cell culture onto a compatible mesh;

(c) inserting said cell-attached mesh into said bottle;

(d) adding a culture medium for said cells to said bottle;

(e) sealing both ends of said bottle, thereby enclosing a first atmosphere within said bottle;

(f) injecting a quantity of a second atmosphere containing said volatile chemical into said bottle through one of said sealing means while simultaneously providing egress for a like quantity of said first atmosphere from said bottle through the other of said sealable means to avoid mixing of said first and second atmospheres;

(g) incubating said cell culture while, rotating said bottle, for a suitable time; and (h) determining the viability of said cell culture.

* * * * *

UNITED STATES PATENT AND TRADEMARK OFFICE
CERTIFICATE OF CORRECTION

PATENT NO. : 5,508,174
DATED : April 16, 1996
INVENTOR(S) : Nicholas J. Del Raso It is certified that error appears in the above-indentified patent and that said Letters Patent is hereby corrected as shown below:

Column 1, line 23, "arc" should read --- are ---.
Column 1, line 65, "scalable" should read --- sealable ---.
Column 3, line 39, "Scaling" should read ---Sealing---.
Column 3, line 61, --- of --- should follow "termination".
Column 4, line 29, "system" should read --- septum ---.
Column 4, line 49, "system" should read --- septum ---.

Signed and Sealed this

Twenty-third Day of September, 1997

Attest:

BRUCE LEHMAN

Attesting Officer

Commissioner of Patents and Trademarks